US00PP13245P2

(12) United States Plant Patent
Lemon

(10) Patent No.: US PP13,245 P2
(45) Date of Patent: Nov. 19, 2002

(54) VARIETY OF GERANIUM NAMED 'GLOBAL CORAL ROSE'

(75) Inventor: David Lemon, Lompoc, CA (US)

(73) Assignee: John Bodger and Sons Company, South El Monte, CA (US)

( * ) Notice: Subject to any disclaimer, the term of this patent is extended or adjusted under 35 U.S.C. 154(b) by 0 days.

(21) Appl. No.: 09/612,860

(22) Filed: Jul. 10, 2000

(51) Int. Cl.[7] ..... A01H 5/00
(52) U.S. Cl. ..... Plt./329
(58) Field of Search ..... Plt./329

*Primary Examiner*—Bruce R. Campell
*Assistant Examiner*—Michelle Kizilkaya
(74) *Attorney, Agent, or Firm*—Fulwider Patton Lee & Utecht, LLP

(57) ABSTRACT

The claimed cultivar is characterized by a red purple semi-double, ruffled, slightly cupped, open, floret further characterized by a lighter reddish area toward base and white at the base of the florets accented with a dark burgundy eye over a medium green cascading mound. The claimed cultivar exhibits high petal retention during final production and shipping with cutting production and rooting speed greatly improved.

1 Drawing Sheet

BACKGROUND OF THE NEW PLANT

The present invention comprises a new and distinct cultivar of *Pelargonium×peltatum* known by the varietal name 'Global Coral Rose' (Oglevee No. 4277, Bodger No. 4 GM297-2). The new variety was discovered in a selective breeding program by David Lemon in Lompoc, Calif. The new variety is a selection from a seed parent of the commercial variety 'Romy' with a pollen parent of a cross between 'Nanette' and 'Cornell' (Bodger No. 2 GM209A light red).

The new cultivar was first asexually reproduced by cuttings in Connellsville, Pa. on Jan. 23, 1995 and has been repeatedly asexually reproduced by cuttings in Connellsville, Pa. It has been found to retain its distinctive characteristics through successive propagations.

The new cultivar, when grown in a glass greenhouse in Connellsville, Pa., using full light, 60° Fahrenheit night temperature, 68° Fahrenheit day temperature, and grown in a soilless media using a constant fertilizer of 200–250 parts per million of Nitrogen and Potassium, in full light. The claimed plant was grown from a rooted cutting, potted in a 10 centimenter pot and exhibited a six week response time from the rooted cutting to a flowering plant.

DESCRIPTION OF THE DRAWING

The accompanying drawing illustrates the new cultivar taken twelve weeks from transplanting into hanging basket, the color being as nearly true as possible with color illustrations of this type.

DESCRIPTION OF THE NEW PLANT

The following detailed desciption sets forth characteristics of the new cultivar. The data which defines each characteristics was collected from asexual reproductions carried out in Connellsville, Pa. The plant histories were taken on rooted cuttings believed to have been potted in a 10 cm pot on approximately Jan. 26, 1998 and flowering on approximately Mar. 30, 1998, under full light in the greenhouse, and color readings were taken in the Oglevee office under 30–40 foot candles of cool white flourescent lighting using The Royal Horticultural Society of London Colour Chart.

THE PLANT

Classification:
- *Botanical.*—*Pelargonium×peltatum.*
- *Commercial.*—Florist's Ivy Geranium 'Global Coral Rose'.

Form: Medium cascading mound.
- *Height.*—13.0–14.0 cm above media surface.
- *Growth.*—Cascading mound.
- *Strength.*—Presents a uniform cascading hanging basket.

Foliage: Medium green; Stalked leaf attachment.

Leaves:
- *Size.*—6.5–8.3 cm across when fully expanded.
- *Shape.*—Reinform with cordate base.
- *Margin.*—Pedately lobed.
- *Texture.*—Pubescent; Leathery.
- *Color.*—Top: Green Group 137A. Bottom: Yellow-Green Group 144A. Zone: None observed.
- *Ribs and veins.*—Palmate venation. Color: Yellow-Green Group 144A.

Petioles:
- *Length.*—2.5–4.7 cm.
- *Color.*—Yellow-Green Group 144A.

Stem:
- *Color.*—Yellow-Green Group 144A.
- *Internode length.*—4.0–5.2 cm.

THE BUD (UMBEL)

Shape: Elongated Elliptical Cluster.
Size: 3.0–3.5 cm across just showing color.
Blooming habit: Continuous blooming; semi-double flowers, duration of bloom time from Spring to first frost.
Borne: Umbel; Florets on pedicel; Pedicel on peduncle.
Closed florets: Bud Size 1.2–1.4 cm long just showing color.
Size: Fully Open Bloom: 8.0–9.7 cm across.
Open florets:
- *Form.*—Ruffled; slightly cupped.
- *Color.*—Top: Red-Purple Group 66A with a lighter area toward base of Red Group 55B with white at base.

Some with darker veining areas of Red Group 52A. Bottom: Outer edge is Red Group 55B with lighter area of Red Group 55D near center. Base is white. Eye: Dark eye and veining of Red-Purple Group 61A present on upper petals with a lighter are of pale pink in the center.

*Petals.*—7–10 in number.

*Size.*—2.5–3.0 cm long; 1.2–1.6 cm across.

*Texture and appearance.*—Highly reflective; smooth and velvety.

Petaloids:

*Quantity.*—0–4 petaloids.

*Shape.*—Irregular; Twisted, tubular, cut edges.

*Color.*—Top: Red-Purple Group 66A. Bottom: Red Group 55D.

Pedicel:

*Length.*—2.5–3.3 cm.

*Color.*—Yellow-Green Group 144A some having touches of Greyed-Purple Group 185A.

Peduncle:

*Length.*—10.0–19.0 cm.

*Color.*—Yellow-Green Group 144A.

Persistence:

*Disease resistance.*—Not known.

*Lasting quality.*—Holds petals well during final stages of production and shipping to the retail seller.

REPRODUCTIVE ORGANS

Stamens:

*Anthers.*—Length: 2.0–3.0 mm.

*Filaments.*—Length: 0.9–1.1 cm. Color: White with pink tips.

*Pollen.*—Golden Orange.

Pistils:

*Number.*—1, 5–6 parted.

*Length.*—1.0–1.5 cm.

*Stigma.*—Color: Pink.

*Style.*—Length: 5.0–7.0 mm.

Ovaries:

*Color.*—Green.

*Length.*—5.0–6.0 mm.

Fruit: None observed.

GENERAL CHARACTERISTICS

Global Coral Rose adds a new and distinct color to the Global series. The bright coral rose flowers are accented with a dark burgundy eye above a mound of medium green foliage. This variety exhibits good cutting production, medium rooting speed, quick sizing to fill up a hanging basket as well as good post harvest qualities. This variety could be compared to Sybil Holmes, the color is slightly different but the flowers open fully and cutting production and rooting speed is greatly improved.

I claim:

1. A new and distinct variety of Geranium plant, substantially as shown and described.

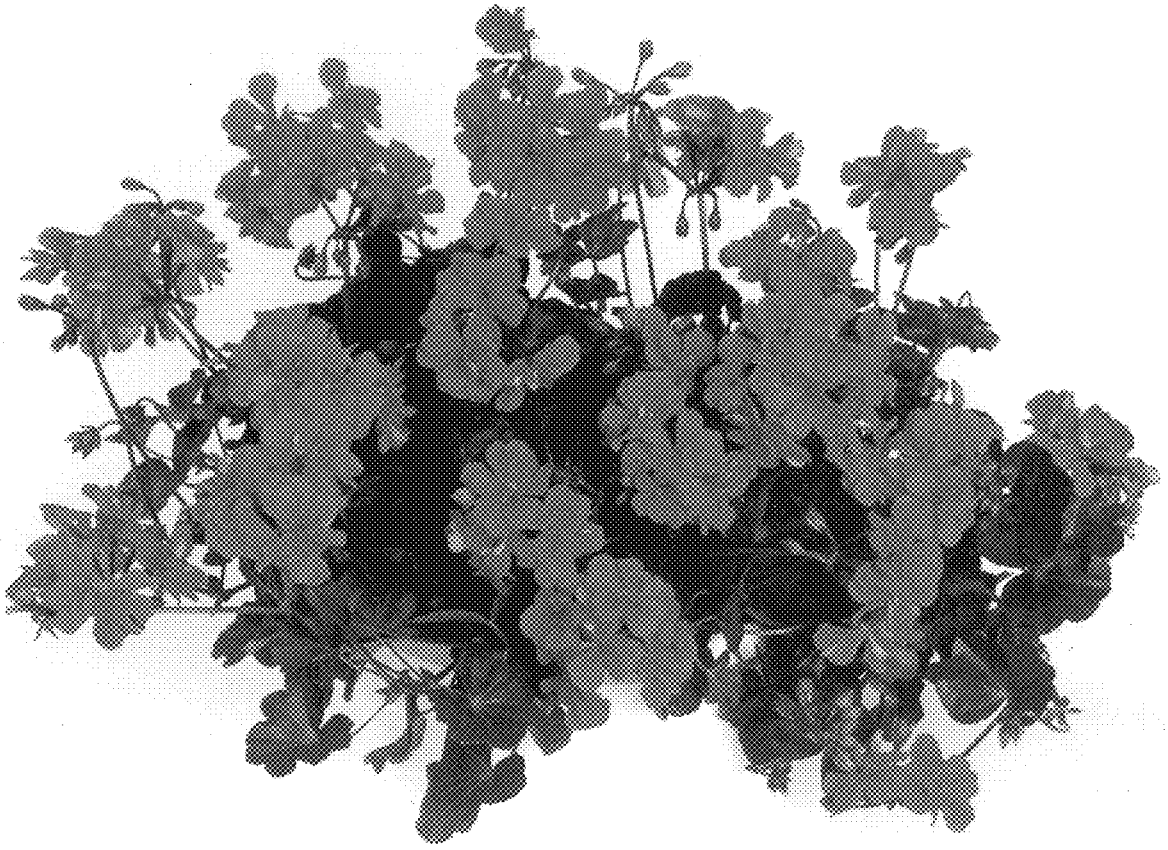

* * * * *